United States Patent [19]

Nishioka et al.

[11] Patent Number: 5,138,029
[45] Date of Patent: Aug. 11, 1992

[54] BIODEGRADABLE OR BIOCOMPATIBLE COPOLYMER AND PROCESS FOR PRODUCING SAME

[75] Inventors: Masaaki Nishioka; Hidemitsu Takinishi; Shiro Fukuyama, all of Tokyo; Atsuo Nishimura; Hiromi Niitsu, both of Kawasaki, all of Japan

[73] Assignee: Showa Denko K.K., Tokyo, Japan

[21] Appl. No.: 725,099

[22] Filed: Jul. 3, 1991

[30] Foreign Application Priority Data

Jul. 6, 1990 [JP] Japan .................. 2-179170

[51] Int. Cl.$^5$ .................. C12P 7/62; C08G 63/06; C12R 1/05
[52] U.S. Cl. .................. 528/354; 435/42; 435/135; 435/822; 435/829; 528/355; 528/359; 528/361; 528/491
[58] Field of Search .............. 435/42, 135, 822, 829, 435/; 528/361, 354, 355, 359, 491

[56] References Cited

U.S. PATENT DOCUMENTS

| | | | |
|---|---|---|---|
| 4,393,167 | 7/1983 | Holmes . | |
| 4,477,654 | 10/1984 | Holmes | 528/361 |
| 4,997,909 | 3/1991 | Doi | 528/361 |

FOREIGN PATENT DOCUMENTS

| | | |
|---|---|---|
| 0069497 | 1/1983 | European Pat. Off. . |
| 0304293 | 2/1989 | European Pat. Off. . |
| 57-150393 | 9/1982 | Japan . |
| 58-69224 | 4/1983 | Japan . |
| 59-220192 | 12/1984 | Japan . |
| 63-226291 | 9/1988 | Japan . |
| 63-269989 | 11/1988 | Japan . |
| 64-48821 | 2/1989 | Japan . |

OTHER PUBLICATIONS

Applied and Environmental Microbiology, vol. 54, No. 8 (1988), pp. 1977-1982.
Macromolecules, 22, (1989), pp. 1106-1115.
P. A. Holmes, "Biologically Produced (R)-3-Hydroxyalkanoate Polymers and Compolymers" Developments in crystalline polymers-2 P.1-P. 65 (1988) by D. C. Bassett, Elsevier Applied Science Publishers Ltd.
R. M. Latferty et al., "Microbial Production of Poly-β-Hydroxybutyric Acid", Biotechnology vol. 6b (1988) pp. 135-176, by H. J. Rehm and G. Reed.
*Makromolekulare Chemie, Macromolecular Chemistry and Physics*, vol. 8, No. 12 (1987), pp. 631-635 European Search Report.
Derwent Abs 86-327239/50 Senior et al. Abs EP-204442 (Dec. 1986).
Derwent Abs 84-184001/30 Richardson Abs EP-114086 (Jul. 1984).

*Primary Examiner*—Herbert J. Lilling
*Attorney, Agent, or Firm*—Sughrue, Mion, Zinn, Macpeak & Seas

[57] ABSTRACT

A random copolymer comprising, as repeating units,
(i) 20 to 90 mol % of 3-hydroxybutyrate unit (3HB) having the formula (I):

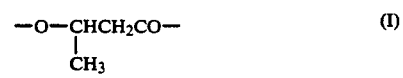

(ii) 5 to 70 mol % of 3-hydroxyvalerate unit (3HV) having the formula (II):

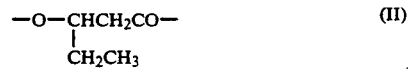

and
(iii) 1 to 15 mol % of 4-hydroxyvalerate unit (4HV) having the formula (III):

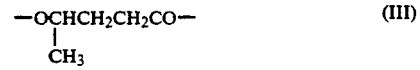

wherein the total of the units 3HB, 3HV, and 4HV is 100 mol %, and having a weight average molecular weight within the range of from 10,000 to 2,500,000 and a production process thereof.

6 Claims, No Drawings

BIODEGRADABLE OR BIOCOMPATIBLE COPOLYMER AND PROCESS FOR PRODUCING SAME

BACKGROUND OF THE INVENTION

1. Field of the Invention

The present invention relates to a novel copolymer produced by using a microorganism, and a process for producing the same. More specifically, it relates to a novel terpolymer comprising 3-hydroxybutyrate units (hereinafter sometimes abbreviated as 3HB), 3-hydroxyvalerate units (hereinafter sometimes abbreviated as 3HV), and 4-hydroxyvalerate units (hereinafter sometimes abbreviated as 4HV), and a process for producing the same.

2. Description of the Related Art

Since poly-3-hydroxybutyrate (PHB) is accumulated within cells of a large number of microorganisms, as an energy storing substance, and is a thermoplastic polymer exhibiting an excellent biodegradability and biocompatibility, it has attracted attention as a "clean" plastic which protects the environment. Particularly, under the present situation in which synthetic plastics are a serious social problem, from the standpoints of environmental pollution and resource circulation, PHB also has attracted attention as a biopolymer which does not depend on petroleum.

For example, PHB can be applied for medical materials such as surgical thread or broken bone setting materials, hygienic articles such as diapers or sanitary articles, agricultural or horticultural materials such as mulch films, slow release chemicals, fishery materials such as fishing nets, packaging materials, and in many other fields.

Nevertheless, PHB has mechanical problems in that it has a high crystallinity (70% or more) and a poor flexibility and can be worked only with difficulty, since it is thermally decomposed at a temperature of the melting point (180° C.) thereof or higher, and has a poor impact resistance. Further, because of a high production cost thereof, PHB has not been industrially produced on a practical scale.

Recently, studies have been made into the use of a copolymer basically comprising a 3-hydroxybutyrate (3HB) unit, and a process for the production thereof using *Alcaligenes eutrophus*.

For example, a copolymer comprising 3HB and 3-hydroxyvalerate units (3HV) is disclosed in (e.g., Japanese Unexamined Patent Publications (Kokai) Nos. 57-150393, 58-69224, 59-220192, 63-269989 and 64-69622.

The introduction of the 3HV component into the copolymer lowers the crystallinity and improves the flexibility of the same. Nevertheless, this copolymer still has problems in that the melting temperature is largely varied. For example, as the content of the 3HV component is increased from zero to 33 mol %, the melting temperature is rapidly lowered from 180° C. to 85° C. (see T. L. Bluhm et al., Macromolecules, 19, 2871–2876 (1986)), and therefore, it becomes difficult to industrially produce uniform products. This copolymer has other problems in that valeric acid, which is expensive, is used as a carbon source (Japanese Unexamined Patent Publication (Kokai) Nos. 63-269989 and 64-69622); and the production process is complicated (Japanese Unexamined Patent Publication (Kokai) No. 59-220192).

The terpolymer (or three unit copolymer) wherein, in addition to the above-mentioned 3HB and 3HV, a 5-hydroxyvalerate unit (5HV) is introduced as a third component is disclosed in Japanese Unexamined Patent Publication (Kokai) No. 64-48820, and the terpolymer wherein a 3-hydroxypropionate unit (3HP) is introduced as a third component is disclosed in Japanese Unexamined Patent Publication (Kokai) No. 58-69224.

The former terpolymer has a problem in that, although the melting point thereof is as low as about 100° C., the effect of the melting point due to the introduction of the 5HV component is not observed because the melting point thereof is not substantially different from a copolymer composed of 3HB and 3HV containing the same mol % of 3HV. Further, also in the production thereof, 5-chloro-valeric acid used as a carbon source is expensive, and the polymer content in the microorganism cells is low.

The latter terpolymer has a high melting temperature of 170° to 172° C., and at a temperature higher than this temperature, it is easily thermally decomposed, and therefore, problems arise during a melt molding thereof.

Japanese Unexamined Patent Publication (Kokai) Nos. 64-48821 and 1-222788 disclose a copolymer comprising 3HB and a 4-hydroxybutyrate unit (4HB). These copolymers have a drawback such that the melting temperatures thereof are 156 to 159° C., and thus a thermal decomposition during a thermal melt molding thereof occurs.

As described above, a practical thermoplastic copolymer having a flexibility, an excellent moldability, biodegradability and biocompatibility characteristics, and which is not thermally decomposed, is easily moldable and is produced by microorganisms, as well as a process for producing the same, are not conventionally known.

Japanese Unexamined Patent Publication (Kokai) No. 58-69224 teaches that the 4-hydroxyvalerate unit (4HV) used in the present invention can be introduced into a copolymer from 4-hydroxyvaleryl coenzyme A (i.e., CoA), which is derived from a condensation and reduction of acetyl CoA and acryl CoA or a condensation and dehydration of 3-hydroxy or 3-chloropropionate and acetyl CoA. Nevertheless, there are no specific descriptions of a copolymer containing a 4-hydroxyvalerate unit (4HV) in this publication, although only a possibility thereof is vaguely suggested.

SUMMARY OF THE INVENTION

Accordingly, the objects of the present invention are to eliminate the above-mentioned disadvantages of the prior art and to provide a practical copolymer produced by a microorganism and which has biodegradability or biocompatibility characteristics, and further, has a required flexibility, is not thermally decomposed during molding, is sufficiently resistant to the heat of, for example, a thermal disinfection, and has an excellent moldability.

Other objects and advantages of the present invention will be apparent from the following description.

In accordance with the present invention, there is provided a random copolymer comprising, as repeating units, (i) 20 to 90 mol % of a 3-hydroxybutyrate unit (3HB) having the formula (I):

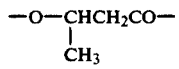

(ii) 5 to 70 mol % of a 3-hydroxyvalerate unit (3HV) having the formula (II):

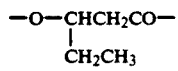

and
(iii) 1 to 15 mol % of a 4-hydroxyvalerate unit (4HV) having the formula (III):

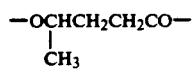

wherein the total of the units 3HB, 3HV, and 4HV is 100 mol %, and having a weight average molecular weight of from 10,000 to 2,500,000.

In accordance with the present invention, there is also provided a process for producing the above-mentioned random copolymer, comprising culturing a microorganism capable of producing a polyhydroxyalkanoate in the presence of τ-valerolactone, to form and accumulate a random copolymer comprising the above mentioned 3-hydroxybutyrate units (3HB), 3-hydroxyvalerate units (3HV), and 4-hydroxyvalerate units (4HV) within the microorganism cells, followed by recovering the same.

DESCRIPTION OF THE PREFERRED EMBODIMENTS

The present inventors have conducted extensive studies and research into the obtaining of a copolymer having various properties, particularly biodegradability and biocompatibility characteristics, and as a result, found that, by using τ-valerolactone, a microorganism is cultured which is conventionally known to have a polyhydroxyalkanoate production ability, whereby a novel three-unit random copolymer (or terpolymer) containing 3HB, 3HV and 4HV units is generated and accumulated within cells of the microorganism, and that the 4HV-unit-containing copolymer thus obtained is a low melting point type copolymer having an excellent moldability.

The present invention will be illustrated in detail as follows.

Microorganism

Any microorganisms capable of producing polyhydroxyalkanoates such as polyhydroxybutyrate (PHB) can be used. Practically, for example, *Alcaligenes faecalis, Alcaligenes ruhlandii, Alcaligenes latus, Alcaligenes aguamarinus* and *Alcaligenes eutrophus* can be used.

Furthermore, a mutant strain obtained by an artificial mutation treatment of these strains and a strain similar to said strains but obtained by a gene -engineering technique can be used.

As typical examples of the strain belonging to these genera, mention may be made of *Alcaligenes faecalis* ATCC 8750, *Alcaligenes ruhlandii* ATCC 15749, *Alcaligenes latus* ATCC 29712, *Alcaligenes aguamarinus* ATCC 14400 and *Alcaligenes eutrophus* H-16 ATCC 17699, *Alcaligenes eutrophus* NCIB 11597, NCIB 11598, NCIB 11599 and NCIB 11600, which are the mutant strains of the H-16 strain.

Among the above, in view of the practical use thereof, *Alcaligenes eutrophus* H-16 ATCC 17699 and *Alcaligenes eutrophus* NCIB 11599 are particularly desirable.

The bacteriological properties of these microorganisms belonging to the genus Alcaliqenes are described in, for example, "BERGEY's MANUAL OF DETERMINATIVE BACTERIOLOGY, Eighth Edition, The Williams & Wilkins Company/Baltimore", and further, the bacteriological properties of *Alcaligenes eutrophus* H-16 are described in, for example, "J. Gen. Miclobiol., 115, 185-192 (1972)", respectively.

Cultivation Method

As in the conventional methods, these microorganisms are cultured according to the two step process. These two steps are a first cultivation step for the growth of microorganism cells, and a second cultivation step for the generation and accumulation of a copolymer within microorganism cells while restricting the components necessary for the growth of microorganism cells such as nitrogen, phosphorus, or oxygen.

First step cultivation

For the cultivation in the first step, the conventional cultivation method of growing microorganisms is applicable, i.e., a medium and cultural conditions in which the microorganism to be used can be grown may be employed.

The culture medium components are not particularly limited, provided that they are substances which can be utilized by the microorganism to be used, but in practice, as the carbon sources, there may be employed synthetic carbon sources such as methanol, ethanol and acetic acid, inorganic carbon sources such as carbon dioxide, natural products such as yeast extract, molasses, peptone and meat extract, saccharides such as arabinose, glucose, mannose, fructose and galactose, and sorbitol, mannitol and inositol. As the nitrogen sources, for example, inorganic nitrogen compounds such as ammonia, ammonium salts, nitrates, and/or organic nitrogen containing compounds such as urea, corn steep liquor, casein, peptone, yeast extract, meat extract may be employed.

The inorganic components can be selected, for example, from calcium salts, magnesium salts, potassium salts, sodium salts, phosphoric acid salts, manganese salts, zinc salts, iron salts, copper salts, molybdenum salts, cobalt salts, nickel salts, chromium salts, boron compounds, and iodine compounds.

If necessary, vitamins can be employed.

The cultural conditions are not particularly limited, but the temperature is, for example, about 20 to 40° C., preferably about 25 to 35° C., and the pH is, for example, about 6 to 10, preferably about 6.5 to 9.5. The aerobic cultivation is carried out under these conditions.

When the cultivation is carried out in a range outside such conditions, the growth of the microorganism may be relatively poor, but the cultivation in a range outside such conditions will not be obstructed.

The cultivation system may be either batchwise or continuous.

Second Cultivation Step

The cells obtained in the cultivation by the first step are further cultured under conditions whereby the amount of components necessary for the growth, such as nitrogenous and/or phosphorous source and/or oxygen is restricted.

More specifically, the microorganism cells are recovered by separation, by a conventional solid-liquid separation means such as filtration and centrifugation, from the culture broth obtained in the first step, and the cells thus obtained are subjected to cultivation in the second step. Alternatively, in the cultivation in the previous step, the components necessary for the growth, such as nitrogenous and/or phosphorous source and/or oxygen is substantially depleted, and the culture broth can be directly transferred to cultivation in the second step without a recovery by separation of the cells to be cultured therein.

The cultivation in the second step is the same as the cultivation in the first step, except that substantially no nitrogenous and/or phosphorous source and/or oxygen is contained in the culture medium or the culture broth, and τ-valerolactone is contained as the specified carbon source.

This carbon source is contained in the culture medium as the culture broth of the second cultivation stage. In the latter case, the carbon source may be added at any time during the cultivation, from the initial stage through to the end stage of the cultivation, but an addition at the initial stage is preferable.

The τ-valerolactone may be used in an amount which can generate a copolymer and does not inhibit the growth of a microorganism, and usually is used in an amount of about 5 to 200 g, preferably 10 to 160 g, per 1 l of a culture medium or a culture broth. The τ-valerolactone can be added all at once to the culture medium or a culture broth, or can be added continuously or semi-continuously as the τ-valerolactone is consumed.

Other carbon sources utilizable by the microorganism employed, such as glucose, fructose, methanol, ethanol, acetic acid, propionic acid, butyric acid, and lactose, also can be permitted to coexist in small amounts. However, the use of these carbon sources, which produces acetyl CoA by an ordinary metabolism, tends to increase the 3-hydroxybutyrate unit (3HB) and accordingly, to decrease the 3HV and 4HV units in the copolymer.

Separation of Microorganism Cells and Copolymer

From the culture broth thus obtained, the microorganism cells are recovered by separation by a conventional solid-liquid separation means such as filtration and centrifugation, and the cells are washed and dried to obtain dry cells. The copolymer formed is extracted from the dry cells or the wet cells in a conventional manner, for example, by extraction with an organic solvent such as chloroform, and to the extract is added, for example, a poor solvent which does not readily dissolve the copolymer such as hexane, to thereby precipitate the copolymer. Alternatively, separated and recovered microorganism cells are treated with chemicals such as sodium hypochlorite which can solubilize the microorganism cells, or with an enzyme and/or a surfactant, to thereby solubilize the cell membrane and the cytoplasm of the microorganism cells, and the copolymer granules are then recovered by separation by a conventional solid-liquid separation means such as filtration or centrifugal separation, followed by washing and drying the copolymer.

Properties of Copolymer

The copolymer thus obtained is a three-unit random copolymer containing a novel 4-hydroxyvalerate unit (4HV) wherein 3HB, 3HV, and 4HV components form ester bonds with each other.

The molecular weight and the ratio of each component can be controlled by changing the kind of microorganism used, and the kind or concentration of the carbon source (τ-valerolactone and other carbon sources). The proportion of the 4HV component can be controlled by increasing or decreasing the proportion of the τ-valerolatone in the total carbon sources. When the proportion of the τ-valerolactone is increased, the amount of the 4HV component can be increased. As the increase in the proportion of the 4HV component, the proportion of the 3HV component tends to increase, but that of the 3HB component tends to decrease.

The terpolymer according to the present invention comprises 20 to 90 mol %, preferably 20 to 85 mol %, of a 3HB component, 5 to 70 mol %, preferably 13 to 65 mol %, of a 3HV component, 1 to 15 mol %, preferably 2 to 15 mol %, of a 4HV component (the total of each component is 100 mol %), has a weight average molecular weight of 10,000 to 2,500,000, particularly 100,000 to 1,500,000. Further, the copolymer has a melting temperature of 50 to 70° C., which is not widely varied even when the proportion of a 4HV component is changed and therefore, can be fabricated at a low melt molding temperature, and in addition, has a heat-resistance high enough to allow a thermal disinfection to be effected, and the melt molding can be easily carried out and is advantageous from an energy viewpoint. Furthermore, there are no deterioration problem due to a thermal decomposition.

EXAMPLES

The present invention will now be further illustrated by, but is by no means limited to, the following Examples.

Example 1

A copolymer was prepared by using *Alcaligenes eutrophus* ATCC 17699.

First cultivation step

First, 2 liters of a medium E having the following composition were introduced into a 5-liter jar fermenter, and the above-mentioned microorganism was aerobically cultured at a pH of 7 to 8 and a temperature of 30° C. for 24 hours. During the cultivation, the fructose was replenished in accordance with the consumption of the same. Thereafter, the microorganism cells were centrifugally separated.

The medium E was composed of the following components:

| | |
|---|---|
| $(NH_4)_2SO_4$ | 5 g |
| $K_2HPO_4$ | 8 g |
| $KH_2PO_4$ | 1 g |
| NaCl | 0.5 g |
| $MgSO_4$ | 2.5 g |
| Mineral solution* | 20 ml |
| Fructose | 15 g |
| Deionized water | 1 l |

The pH was automatically adjusted by using aqueous NaOH and $H_2SO_4$ solutions.

The above-mentioned mineral solution* comprised the following components:

| | |
|---|---|
| FeSO$_4$ | 5 g |
| CaCl$_2$ | 10 g |
| MnSO$_4$ | 1 g |
| CuSO$_4$ | 100 mg |
| ZnSO$_4$ | 500 mg |
| CoCl$_2$ | 100 mg |
| MoO$_3$ | 1 mg |
| H$_3$BO$_3$ | 1 mg |
| Aqueous 0.1 N—HCl solution | 1 l |

Second cultivation step

The microorganism cells obtained in the first cultivation step were suspended at a concentration of about 10 g/l in a medium F and shaken cultured in a 500 ml flask at a temperature of 30° C. for 48 hours. The medium F was composed of the following components and was adjusted at a pH of 7.5.

| | |
|---|---|
| KH$_2$PO$_4$ | 5 g |
| K$_2$HPO$_4$ | 5 g |
| MgSO$_4$ | 1 g |
| Mineral solution* | 2 ml |
| τ-Valerolactone | 20 g |
| Ion-exchanged water | 1 l |

Separation of Microorganism Cells

After the second cultivation step, microorganism cells were separated by centrifugal separation from the culture broth thus obtained, the resultant cells were vacuum dried, and 11.2 g/l of the dried cells was obtained.

Separation and recovery of copolymer

From the dry cells thus obtained, the copolymer was extracted with hot chloroform, precipitated by an addition of hexane to the extract, and the precipitates were subjected to filtration and drying, to give 18.2% by weight of the copolymer based on the weight of the dried microorganism cells.

Characteristics of copolymer

The composition, the molecular weight, and the melting temperature of the copolymer thus obtained were measured as described below:

Composition: $^{13}$C-NMR spectrum and $^1$H-NMR spectrum

Molecular weight: Gel permeation chromatography (GPC) measurement

Melting temperature (Tm): Differential scanning calorimeter (DSC) measurement

The results are shown in Table 1.

The positions to which each carbon atom and hydrogen atom of the copolymer belongs were determined from $^{13}$C-NMR and $^1$H-NMR spectrum are shown in Table 2.

Table 3 shows the diad chain distribution of each component, estimated from the multiple-overlapped line resonance structure of a carbonyl carbon on the basis of Y. Doi. et al., Macromolecules, 19, 2860–2864(1986). This chain distribution shows that the copolymer has a random copolymer chain distribution.

Examples 2

The second step cultivation was also carried out in a 5-liter jar according to Example 1. In the first step cultivation, fructose was additionally added depending upon the consumption of the fructose. In the second step cultivation, τ-valerolactone was directly added such that the initial concentration in the cultivation broth was 1% and additionally added depending upon the consumption of τ-valerolactone. Finally, 120 g/l of medium of τ-valerolactone was gradually, added and the cultivation time was 48 hurs. The dried microorganism cell thus obtained was 59.2 g/l and the content of the copolymer in the dried microorganism cell was 54.1% by weight.

The determination results and the like are shown in Table 1.

Examples 3–5

Example 2 was repeated, except that butyric acid was present in a proportion shown in Table 1, together with the τ-valerolactone as a carbon source.

The determination results and the like are shown in Table 1.

TABLE 1

| Example | Carbon source Sort | g/l*1 | Weight of dry cells g/l*1 | Copolymer content in dry cells % | Copolymer composition mol % [3HB] | [3HV] | [4HV] | Molecular weight*2 Mw × 10$^4$ | Mw/Mn | Melting temperature Tm °C. |
|---|---|---|---|---|---|---|---|---|---|---|
| Example 1 | τ-valerolactone | 20 | 11.2 | 18.2 | 34.4 | 57.6 | 8.0 | 100.4 | 1.45 | 66.4 |
| Example 2 | τ-valerolactone | 120 | 59.2 | 54.1 | 23.9 | 62.6 | 13.5 | 112.4 | 2.18 | 64.9 |
| Example 3 | τ-valerolactone butyric acid | 108 12 | 58.6 | 54.1 | 43.8 | 52.1 | 4.1 | 88.5 | 1.43 | 51.5 |
| Example 4 | τ-valerolactone butyric acid | 90 30 | 61.4 | 41.9 | 74.3 | 23.1 | 2.6 | 66.5 | 1.29 | 53.2 |
| Example 5 | butyric acid | 120 | 63.7 | 39.8 | 100 | 0 | 0 | 59.0 | 1.26 | 178.0 |

*1 g/l- Medium (culture broth)
*2 Mw: Weight average molecular weight
Mn: Number average molecular weight

TABLE 2

| Number *1 | ppm C*2 | H*3 |
|---|---|---|
| 1 | 169.10 | — |
| 2 | 40.94 | 2.49, 2.56 |
| 3 | 67.77 | 5.24 |
| 4 | 19.79 | 1.28 |
| 5 | 169.40 | — |
| 6 | 38.80 | 2.49, 2.56 |
| 7 | 72.06 | 5.15 |
| 8 | 26.87 | 1.64 |
| 9 | 9.31 | 0.90 |
| 10 | 172.20 | — |
| 11 | 30.53 | 2.30 |
| 12 | 31.04 | 1.86 |
| 13 | 70.50 | 4.92 |

TABLE 2-continued

| Number *1 | ppm | |
|---|---|---|
| | C*2 | H*3 |
| 14 | 19.79 | 1.21 |

*1 Corresponds to the encircled numerals described in the following structural formula.
*2 Carbon atoms corresponding to each encircled numeral position described in the following structural formula, determined from $^{13}$C-NMR spectrum.
*3 Hydrogen atoms bound with carbon atoms corresponding to each encircled numeral position described in the following structural formula determined from $^1$H-NMR spectrum.

Structural formula

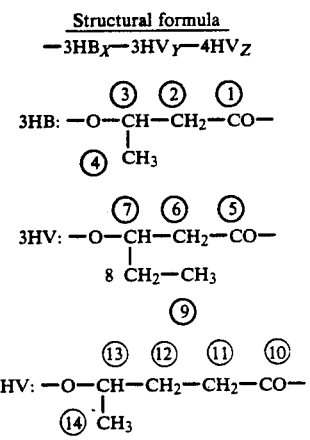

TABLE 3

| Diad | | 3HB-3HB | 3HB-3HV | 3HB-4HV | 3HV-3HV | 3HV-4HV | 4HV-3HB | 4HV-3HV | 4HV-4HV |
|---|---|---|---|---|---|---|---|---|---|
| Chain distribution (%) | Found* | 11.9 | 38.7 | 37.4 | 5.1 | 2.1 | 4.0 | | 0.8 |
| | Calculated*2 | 11.8 | 39.6 | 35.9 | 4.6 | 2.8 | 4.6 | | 0.7 |

*Determined from $^{13}$C-NMR spectrum
**Chain distribution expected in the case of a random copolymer The novel copolymer containing the 4HV component can be easily obtained according to the present invention. Furthermore, the melting point of the copolymer according to the present invention is not largely changed and is as low as 50 to 70° C., even when the proportion of the 4HV content is varied, and therefore, the melt molding temperature can be set at a low temperature. This provides advantages such that the melt molding is very easy the use of energy in reduced, and the problems of a deterioration due to heat decomposition do not arise.

In the bipolymer composed of 3HB and 3HV mentioned as the prior art above (see Japanese Unexamined Patent Publication (Kokai) No. 63-69662, Example 3; Japanese Unexamined Patent Publication (Kokai) No. 64-69622, Example 1), the melting point was lowered from 180° C. of PHB to 100–105° C., even when 56–61 mol % of 3HV is incorporated thereinto. Further, in the case of a terpolymer of 3HB, 3HV and 5HV (Japanese Unexamined Patent Publication (Kokai) No. 64-48820, Example 2), it is shown that, in 63 mol % of the 3HV component and 11 mol % of the 5HV component, the melting point is 101° C., but in the present invention, the melting temperature is further lowered whereby the thermal molding can be carried out without problems. Thus, it can be considered that the 4HV component content makes a considerable contribution to the drop in the melting temperature.

In the production process of the copolymer according to the present invention, advantages are sained such that the terpolymer containing a novel 4HV component can be produced by using, as a sole carbon source, τ-valerolactone, and that the cultivation process is simple and production control of the is easy. Furthermore, in the conventional production processes of a copolymer using a microorganism, usually the yield of the microorganism cell is as low as less than 10 grams/l. In the present invention, however, a higher yield of the microorganism cell of up to 70 grams/l is obtained and the copolymer content in the microorganism cells is high. Therefore, the present process is industrially advantageous.

The coplymer of the present invention having an excellent moldability is expected to be able to be applied for medical materials such as surgical thread, broken bone setting materials, etc., hygienic materials such as diapers, sanitary articles, etc., agricultural and horticultural materials such as mulch films, slow release chemicals, etc., fishery materials such as fishing nets, etc., packaging materials, and others.

We claim:

1. A random copolymer comprising, as repeating units,
(i) 20 to 90 mol % of 3-hydroxybutyrate unit (3HB) having the formula (I):

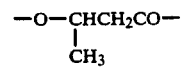   (I)

and (ii) 5 to 70 mol % of 3-hydroxyvalerate unit (3HV) having the formula (II):

   (II)

(iii) 1 to 15 mol % of 4-hydroxyvalerate unit (4HV) having the formula (III):

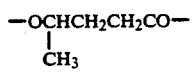   (III)

wherein the total of the units 3HB, 3HV, and 4HV is 100 mol %, and having a weight average molecular weight within the range of from 10,000 to 2,500,000.

2. A random copolymer as claimed in claim 1, wherein the copolymer comprises (i) 20 to 85 mol % of 3HB, (ii) 13 to 65 mol % of 3HV, and (iii) 2 to 15 mol % of 4HV.

3. A random copolymer as claimed in claim 1, wherein the weight average molecular weight of the random copolymer is 100,000 to 1,500,000.

4. A process for producing a random copolymer according to claim 1, comprising culturing a microorganism in the presence of at τ-valerolactone to form and accumulate a random copolymer comprising 3-hydroxybutyrate units (3HB), 3-hydroxyvalerate units (3HV), and 4-hydroxyvalerate units (4HV) within the microorgani cells, followed by recovering the same wherein said microorganism belongs to the genus Alcaligenes.

5. A process as claimed in claim 4, wherein said microorganism is at least one member selected from the group consisting of those belonging to *Alcaligenes facecalis, Alcaligenes ruhlandii, Alcaligenes latus, Alcaligenes aguamarinus* and *Alcaligenes eutrophus.*

6. A process as claimed in claim 4, wherein said culturing is aerobically effected under the conditions of a temperature of 20° to 40° C. and a pH of 6 to 10.

* * * * *